(12) United States Patent
Revel

(10) Patent No.: US 6,482,447 B2
(45) Date of Patent: *Nov. 19, 2002

(54) METHOD AND COMPOSITION FOR THE TREATMENT OF BENIGN PROSTATE HYPERTROPHY (BPH) AND PREVENTION OF PROSTATE CANCER

(75) Inventor: Chase Revel, Nevis (KN)

(73) Assignee: Glenn Braswell, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/884,622

(22) Filed: Jun. 18, 2001

(65) Prior Publication Data

US 2002/0001632 A1 Jan. 3, 2002

Related U.S. Application Data

(62) Division of application No. 09/658,248, filed on Sep. 8, 2000.
(60) Provisional application No. 60/153,322, filed on Sep. 10, 1999.

(51) Int. Cl.$^7$ ............................................. A61K 35/78
(52) U.S. Cl. ........................ 424/727; 424/41; 424/74; 424/277.1; 424/474; 424/725; 514/2; 514/22; 514/23; 514/70; 514/71; 514/74
(58) Field of Search .......................... 424/41, 74, 725, 424/277.1, 474; 514/2, 22, 23, 70, 71, 74

(56) References Cited

U.S. PATENT DOCUMENTS

| 5,654,011 A | 8/1997 | Jackson et al. ............. 424/635 |
| 6,187,811 B1 | 2/2001 | Lane ........................... 514/458 |

FOREIGN PATENT DOCUMENTS

| EP | 0-600544 A1 | 6/1994 | .......... A61K/31/07 |

OTHER PUBLICATIONS

Peumans, W.J. et al., An unusual lectin from stinging nettle (*Urtica dioica*) rhizomes. 1983. FEBS 177:99–103.*
Buck, A.C., British J. Urology, 1996, 78:325–336.
PDR for Herbal Medicines, Medical Economics Company, Montvale, NJ, 1998, pp. 902–903.
Aito, K. et al. "The conservative treatment of prostatic–hypertrophy with Paraprost," Hinyokika Kiye 18(1):41–4 (1972) Abstract.
Mahajan, S.K. et al. "Zinc deficiency: a reversible complication of uremia," The American Journal of Clinical Nutrition 36:1177–1183 (1982).
Wallace, A.M. et al. "Effect of Zinc on Androgen Metabolism in the Human Hyperplastic Prostate," Biochemical Society Transactions 3:540–542 (1975).
Buck, A.C. et al. "Treatment of Chronic Prostatitis and Prostatodynia with Pollen Extract," British Journal of Urology 64:496–499 (1989).
Rugendorff, E.W. et al. "Results of Treatment with Pollen Extract (Cernilton® N) in Chronic Prostatitis and Prostatodynia," British Journal of Urology 71:433–438 (1993).
Habib, F.K. et al. "In vitro Evaluation of the Pollen Extract, Cernitin T–60, in the Regulation of Prostate Cell Growth," British Journal of Urology 66:393–397 (1990).
Zhang, X. et al. "Isolation and Characteristics of a cyclic Hydroxamic Acid from a Pollen Extract, Which Inhibits Cancerous Cell Growth in Vitro," J. Med. Chem. 38:735–738 (1995).
Simon, H.B. "On Call," Harvard Men's Health Watch 4(9):8 (2000) Abstract.
Fahim, M.S. et al. "Chemical sterilization in the male part I: rats," Archives of Andrology 9(3):261–5 (1982) Abstract.
Key, T.J. et al. "A case–control study of diet and prostate cancer," Brit.J.Cancer 76(5)678–87 (1997) Abstract.
Bender, D.A. et al. "Effects of vitamin B6 deficiency and repletion on the uptake of steroid hormones into uterus slices and isolated liver cells of rats," Brit.J.Nutrition 61(3):619–28 (1989) Abstract.
Olson, K.B. et al. "Vitamins A and E: Further Clues for Prostate Cancer Prevention," Journal of the National Cancer Institute 90(6):414–5 (1998).
Bayne, C.W. et al. "*Serenoa repens* (Permixon®): A 5a–Reductase Types I and II Inhibitor–New Evidence in a Coculture Model of BPH," The Prostate 40:232–241 (1999).
Wilt, T.J. et al. "Saw palmetto extracts for treatment of benign prostatic hyperplasia: a systematic review," JAMA 280(18):1604–1609 (1998) Abstract.
Delos, S. et al. "Testosterone metabolism in primary cultures of human prostate epithelial cells and fibroblasts," J. Steroid Biochem Mol Biol 55(3–4):375–83 (1995) Abstract.
Shroder, F. "5 alpha–reductase inhibitors and prostatic disease," Clin Endocrinol 41(2):139–147 (1994) Abstract.
Gann, P.H. et al. "Lower Prostate Cancer Risk in Men with Elevated Plasma Lycopene Levels: Results of a Prospective Analysis," Cancer Research 59(6):1225–1230 (1999).
Giovannucci, E. "Tomatoes, Tomato–Based Products, Lycopene, and Cancer: Review of the Epidemiologic Literature," Journal of the National Cancer institute 91(4):317–331 (1999).
Rao, A.V. et al. "Serum and Tissue Lycopene and Biomarkers of Oxidation in Prostate Cancer Patients: A Case–Control Study," Nutrition and Cancer 33(2):159–164 (1999).

(List continued on next page.)

Primary Examiner—Christopher R. Tate
Assistant Examiner—Kailash C Srivastava
(74) Attorney, Agent, or Firm—Sierra Patent Group, Ltd.

(57) ABSTRACT

Compositions comprising lycopene, *Serenoa repens*, *Pygeum africanum*, and *Urtica dioica* are provided. The compositions are preferably formulated with an alcohol extract of the dried, cut plant parts. Methods of using such compositions for treating various conditions and diseases, including benign prostatic hypertrophy and prostate cancer are also provided.

6 Claims, No Drawings

OTHER PUBLICATIONS

Pastori, M. et al. "Lycopene in Association with a–Tocopherol Inhibits at Physiological Concentrations of Proliferation of Prostate Carcinoma Cells," Biochemical and Biophysical Research Communications 250(3):582–585 (1998).

Barlet, A. et al., "Efficacy of *Pygeum africanum* Extract in the Treatment of Micturitional Disorders due to Benign Prostatic Hyperplasia. Evaluation of Objective and Subjective Parameters. A multicenter, randomized, double–blind trial," Wiener Klinishce Wochenschrift 102(22):667–673 (1990).

Carani, C. et al. "Urological and sexual evaulation of the treatment of benign prostate pathology with high doses of *Pygeum africanum*," Arch.Ital.Urol. [Italian Urology Archives] 63:341–345 (1991).

Schottner, M. et al. "Lignans from the Roots of *Urtica dioica* and their Metabolites Bind to Human Sex Hormone Binding Globulin (SHBG)," Planta medica 63:529–532 (1997).

Hryb, D.J. et al. "The Effect of Extracts of the Roots of the Stinging Nettle (*Urtica dioica*) on the Interaction of SHBG with its Receptor on Human Prostatic Membranes," Planta Med. 61:31–32 (1995).

Perrin, P et al. "Circulating prostate cancer specific antigens in benign hypertrophy and localized cancer of the prostate," Presse Med, 20(28):1313–9 (1991) Abstract.

Harvey, H. "A unifying hypothesis that links benign prostatic hyperplasia and prostatic intrepithelial neoplasia with prostate cancer. Invited comments," Pathol Res Pract, 191(9):924–34 (1995) Abstract.

Chattopadhyay, A. et al. "Antitesticular effect of copper chloride in albino rats," J. Toxicological Sciences 24(5):393–7 (1999) Abstract.

* cited by examiner

METHOD AND COMPOSITION FOR THE TREATMENT OF BENIGN PROSTATE HYPERTROPHY (BPH) AND PREVENTION OF PROSTATE CANCER

This application is a Divisional application of Ser. No. 09/658,248, filed Sep. 8, 2000, which claims priority from provisional application No. 60/153,322, filed Sep. 10, 1999.

BACKGROUND OF THE INVENTION

1. Field of the Invention

The invention relates to a method and composition for the treatment and alleviation of symptoms of benign prostatic hypertrophy (BPH) and prevention of prostate cancer.

2. Discussion of Related Art

Prostate cancer is a leading cause of death among men. The American Cancer Society estimates that about 180,400 men will be diagnosed with prostate cancer during 2000. An estimated 31,900 men will die in the year 2000, making prostate cancer the second leading cause of cancer death in men in the United States. Eighty-nine percent of men with prostate cancer live at least five years, and 63% survive at least 10 years. However, if the cancer is found before it has spread outside the prostate, the five year relative survival rate is 100%. If the cancer has spread to tissue near the prostate, the survival rate is 94%. If the cancer has spread to distant parts of the body when it is found, only about 31% will live at least five years.

Studies have shown a correlation between BPH and prostate cancer. Physicians have used the prostate specific antigen (PSA) blood test to test their patients for prostate cancer. The PSA blood test measures the prostate specific antigen made by prostate cells. PSA blood test results are reported as ng/ml. Results under 4 ng/ml are usually considered normal. Results over 10 ng/ml are high and values between 4–10 ng/ml are considered borderline. Conditions such as BPH and inflammation of the prostate (prostatis) can cause high PSA values. In one study to determine the correlation between BPH and prostate cancer, Perrin et al., state that an increase in serum levels of PSA correlates with similar increased levels of PSA in prostate cancers [Perrin P, Francois O, Maquet J H, Bringeon G, Duteil P, Devonec M, (1991) Presse Med 20(28):1313–1319]. Another study states that urethra blockage caused by BPH is responsible for cysts observed in prostate cancer [Harvey, H, (1995) Pathol Res Prac 191(9):924–934]. Therefore, studies support the proposition that treatments to reduce BPH will also reduce the incidence of prostate cancer.

Some of the most common symptoms of BPH include: 1) a need to urinate often (especially disturbing at night); 2) a weak or interrupted urinary stream; 3) a feeling that you cannot empty your bladder completely; 4) a feeling of delay or hesitation when you start to urinate; 5) a feeling that you must urinate right away; and 6) continuing pain in the lower back, pelvis or upper thighs. These symptoms are caused by the way in which BPH affects the urethra and, later, the bladder. If a urinary tract infection develops, there may also be burning or pain during urination. In the early phase of prostatic enlargement, the bladder muscle has to force urine through the narrowed urethra by contracting more forcefully. Over a period of time, the forcing causes the bladder muscle to become stronger, thicker, and overly sensitive. In some cases, as prostate enlargement progresses and the urethra is squeezed more tightly, the bladder cannot overcome the problems created by the greatly narrowed urethra. If this happens, the bladder can not empty completely. This situation creates a need to urinate more frequently. In a small percentage of men, incomplete emptying of the bladder may lead to repeated urinary track infections, sudden inability to urinate, or gradual bladder and/or kidney damage. An enlarged prostate can even result in total blockage of the urethra, a very serious condition.

Symptoms of advanced prostate cancer include: 1) having trouble having or keeping an erection; 2) blood in the urine; 3) swollen lymph nodes in the groin area; and 4) pain in the pelvis, spine, hips, or ribs. Known risk factors for prostate cancers include age, family history, diet and race. After the age of 50, both incidence and mortality from a prostate cancer increase at a nearly exponential rate. For example, more than 75% of all cancers are diagnosed in men over the age of 65. Kupelian et al., have shown that the younger age of an onset of the disease is associated with family history of prostate cancer [Kupelian P A, Klein E A, Witte J S, Kupelian V A, Suh J H, (1997) J of Urol 158(6):2197–2201]. Their studies showed that 18% of patients under age of 65 at the onset of the disease have a positive family history, compared to 6% of those diagnosed with the disease over age 65. Carter et al., showed that the risk of developing the disease increases with the number of affected first-degree relatives [Carter B S, Beaty T H, Steinberg G D, Childs B, Walsh P C, (1992) Proc Natl Academy Science USA 89:3367–3371]. Family history also suggests that a high penetrant allele is responsible for this inherited form of prostate cancer [Carter et al., supra; Walsh P C, Partin A W, (1997) Cancer 80:1871–74; Cooney K A, McCarthy J D, Lange E, Huang L, Miesfeldt S, Montie J E, Oesterling J E, Sandier H M, Lange K, (1997) Natl Cancer Inst 89:955–959]. Moreover, the inherited high penetrant allele suggests an explanation for the higher incidence of prostate cancer among African Americans, compared to other race groups. Prostate cancer is about twice as common among African-American men as it is among white American men. Increased incidence of the disease also exists in North America and northwestern Europe, but the incidence is very low in Asian countries, such as China and Japan, and in Central and South America. A diet high in fat may also play a part in causing prostate cancer.

Recent studies have shown that DNA mutations in certain genes may predispose persons to the disease. One candidate gene, Hereditary Prostate Cancer Gene 1 (HPC1), is situated on the long arm of chromosome 1 [Smith J R, Freije D, Carpten J D, Gronberg H, Xu J, Isaacs S D, Brownstein M J, Bova G S, Guo H, Bujnovszky P, Nusskern D R, Damber J E, Bergh A, Emanueisson M, Kallioniemi O P, Walker-Daniels J, Bailey-Wilson J E, Beaty T H, Meyers D A, Walsh P C, Collins F S, Trent J M, Isaacs W, (1996) Science 274:1371–1374]. This gene has been shown to contribute to prostate cancer [Smith et al., supra; Gronberg H, Smith J, Emanuelsson M, Jonsson B A, Bergh A, Carpten J, Isaacs W, Xu J, Meyers D, Trent J, Damber J E, (1999) Am J of Hum Genet 65(1):134–140]. Another candidate gene is PTEN, a putative protein tyrosine phosphatase. Mutations of PTEN have been detected in various cancer cell lines, including prostate cancer cells lines [Li J, Yen C, Liaw D, Podsypanina K, Bose S, Wang S I, Puc J, Miliaresis C, Rodgers L, McCombie R, Bigner S H, Giovanella B C, Ittmann M, Tycko B, Hibshoosh H, Wigler M H, Parsons R, (1997) Science 275:1943–1947]. Research on HPC1, PTEN, and related genes, is still preliminary and genetic tests and are not known to be available. Therefore, in the absence of a genetic test, early detection, treatment and prevention are the best therapies for prostate cancer.

There is also evidence that the development of prostate cancer is linked to increased levels of hormones, or androgens. Androgens are known to be important in promoting the growth of both normal and cancerous prostate cells. The Prostate Cancer Prevention Trial is a study (currently underway) to determine whether medications to lower androgen levels can reduce prostate cancer. Previous studies have shown that high levels of androgens, more specifically testosterone and conversion of its more active metabolite dihydrotestosterone (DHT), stimulate BPH. BPH is considered to be normal after the age of 45, however, it becomes problematic when the benign tumor begins to obstruct sections of the urethra and interferes with normal urinary discharge.

The use of herbal medicines to treat cancers is an alternative method of treatment. Certain herbal medications tend to have an affinity for particular tumor types and can therefore be selected based on their specific indications. It is estimated that approximately 50 percent of the thousands of drugs commonly used and prescribed today are either derived from a plant source or contain chemical imitations of a plant compound [Mindell, E., Earl Mindell's Herb Bible, A Fireside Book (1992)]. Currently, a number of medicinal formulations contain herbal components or extracts from herbs. Many chemotherapeutic agents such as taxol and vincrinstine are derivatives of botanical or herbal medicines that have successfully treated cancers.

In Europe the use of herbal supplements comprising *Serenoa repens* (saw palmetto) to treat BPH and prostatic cancer is widespread. *Serenoa repens* is a small shrubby palm tree found in the southeastern coastal United States. A recent review of studies completed by Harvard researchers concluded that saw palmetto extract was effective as Proscar® in the treatment of BPH. Many studies have reported *Serenoa repens* acts as a major inhibitor of 5-alpha-reductase [Bayne C W, Donnelly F, Ross M, Habib F K, (1999) Prostate 40(4):232–241; Wilt T J, Ishani A, Stark G, MacDonald R, Lau J, Muirow C, (1998) JAMA 280(18):1604–1609; Delos S, Carsol J L, Ghazarossian E, Raynaud J P, Martin P M, (1995) J Steroid Biochem Mol Biol 55(3–4):375–383; Schroder F, (1994) Clin Endocrinol 41(2):139–147]. 5-alpha-reductase is an enzyme which cleaves testosterone to form 5-alpha-dihydrotestosterone, or DHT. DHT levels in BPH are significantly higher compared to controls. In a recent study, Bayne et al., (supra) showed that a commercial form of *Serenoa repens*, Permixon, was an effective inhibitor of 5-alpha-reductase. This study supports a previous study by Delos et al., (supra) which showed that *Serenoa repens* (Permixon) alone was able to inhibit 5-alpha-reductase activities in both normal primary cultures of epithelial cells and in fibroblasts separated from BPH and prostate cancer tissues. Furthermore, the Bayne et al. study showed that the activity of *Serenoa repens* does not influence the secretion of prostate specific antigen (PSA), permitting the continued use of PSA blood measurements for prostate cancer screening. Additionally, treatments of BPH with *Serenoa repens* in Europe are documented to be well tolerated and appear to have few, if any, significant adverse side effects [Wilt et al., supra].

Many studies have also shown that increased beta-carotenoids reduce the incidences of BPH and prostate cancer. These studies also support the proposition that treatments to reduce BPH will also reduce the incidence of prostate cancer. [Gann P H, Ma J, Giovannucci E, Willett W, Sacks F M, Hennekens C H, Stampfer M J, (1999) Cancer Res 59(6):1225–1230; Giovannucci E, (1999) J Natl Cancer Inst 91(4):317–331; Rao A V, Fleshner N, Agarwal S, (1999) Nutr Cancer 33(2):159–164; Pastori M, Pfander H, Boscoboinik D, Azzi A, (1998) Biochem Biophys Res Commun 250(3):582–585]. Carotenoids are naturally-occurring compounds found abundantly in many plants including tomatoes and tomato products. The major carotenoids are beta-carotene, alpha-carotene, lutein, zeaxanthin, cryptoxanthis, and lycopene. Many studies show that of the major carotenoids, lycopene is the most effective and significant in quenching free oxygen radicals [Gann et al., (supra); Rao et al., (supra); Pastori, et al., (supra); Giovannucci, et al., (supra)]. Free radicals are thought to be involved in the process of many human diseases. Although they may not singly cause the disease, free radicals may predispose conditions for occurrences of such diseases. Free radicals are produced as normal by-products of metabolic processes. They can also originate from environmental pollutants such as nitrogen dioxide, heavy metals, ionizing radiation, and cigarette smoke. They are highly reactive and can damage the structure and functions of cell membranes, nucleic acids and proteins. These damages can result in cell death and mutations of cells, potentially leading to a cancer type situation. Treatment with lycopene, an antioxidant, will reduce free oxygen radicals and therefore reduce BPH, to prevent prostate cancer.

Men with BPH suffer a variety of micturitional disorders, as discussed above. When prostatic tissue becomes enlarged and inflamed there is increased pressure on the urethra, causing micturition dysfunction such as weak or interrupted urine discharge. An herbal supplement from a tree called *Pygeum africanum* has been shown to alleviate many of these symptoms and restore function, as compared to a control group [Barlet A, Albrecht J, Aubert A, Fischer M, Grof F, Grothuesmann H G, Masson J C, Mazeman E, Mermon R, Reichelt H, (1990) Wien Klin Wochenschr 22:667–673; Carani C, Salvioli V, Scuteri A, Borelli A, Baidini A, Granata A R, Marrama P, (1991) Arch Ital Urol Nefrol Androl 63:341–345]. *Pygeum africanum* contains three groups of active lipid-soluble substances: phystosterols, pentacyclic triterpenoids and ferulic esters of fatty acid alcohols. Physterols, particularly, beta-isoterols have been shown to reduce elevated levels of prostaglandins in those suffering from BPH. Reduction in prostaglandins helps to reduce the size of prostate adenomas. The triterpenoids are effective anti edema agents. Lastly, the ferulic esters of fatty acid alcohols help to inhibit the absorption and metabolism of cholesterol. Levels of cholesterol in men suffering from BPH is higher as compared to levels from normal healthy individuals. Additionally, treatments using both *Pygeum africanum* and *Serenoa repens* have been documented in the literature, but each may have different mechanisms of action.

Another symptom of BPH is increased fluid retention. To alleviate this symptom, *Urtica dioica* (common stinging nettle) has been used in the herbal treatment of BPH and prostate cancer. *Utica dioica* has diuretic properties which make it useful for treatment [Varro, T. *Herbs of Choice*, (1994) Pharmaceutical Press]. Also, *Urtica dioica* produces a lectin which to binds to human sex hormone-binding globulin (SHBG) [Schottner M, Gansser D, Spiteller G, (1997) Planta Med 63(6):529–532; Hryb D J, Khan M S, Romas N A, Rosner W, (1995) Planta Med 61(1):31–32]. SHBG is a plasma glycoprotein that binds to circulating plasma steroids (i.e., testosterone, DHT and estradiol), thus regulating plasma levels of free steroids [Rosner W, Hryb D J, Khan M S, Nakhla A M, Romas N A, (1999) J Steroid Biochem Mol Biol 69(1–6):481–485]. *Urtica dioica* lectins binding to SHBG prevents SHBG from binding to its receptors on various sex glands, including the prostate and testes. In the absence of the SHBG ligand, hormone up-take is prevented by glandular cells. Therefore, *Urtica dioica* lectins effectively reduce plasma testosterone. High levels of testosterone and DHT are observed in both BPH and prostate cancer.

The amino acids glycine, alanine and glutamine in combination have also been used successfully to alleviate the urinary symptoms associated with BPH [Damrau, F. (1958) J. Maine Medical Association 49:99–102]. In that study, three months of treatment with this combination resulted in 43–66% improvements in urgency, nocturia, delay in starting the flow, maintenance of flow and frequency. Similar improvements were seen in a Japanese study (Aito, K & Iwatsubo, E (1972) Hinyokika Kiyo—Acta Urologica Japonica. 18(1):41–4), and a single blind study that compared the combination with placebo [Feinblatt, H M & Gant, J (1958), J Maine Medical Assoc. 49:99–124].

Zinc supplementation has been well-established as beneficial to male sexual function. Mahajan, S K, Prasad, A S, Rabbani, P, Briggs, W A & McDonald, F D (1982), Amer J Clin Nutr 36: 1177–1183; Leake, Chisholm & Harib (1984), J Steroid Biochem 20:651–655; Fahim, Wang Sutcu & Fahim (1993), Andrologia 25:369–75, Antoniou, Sudhakar, Shalhoub & Smith (1977), Lancet Oct.: 895–898. Zinc has also been shown to have an inverse relationship with 5 alpha-reductase activity in human prostatic tissue. Wallace, A M, & Grant, J K (1975) Biochemical Society Transactions 3:540–542.

Prostatitis and protatodynia have been treated successfully with bee pollen, Buck A C, Rees, R W M, Ebeling, L (1989), Brit J Urology 64:496–499, Rugendorff, E W et.al. (1993), Brit J. Urology 71:433–438. In vitro studies on the inhibition of cancerous cell growths have demonstrated a beneficial effect of bee pollen. Habib, F K (1990), Brit J Urology 66:393–397; Zhang, X (1995) J Med Chem 38:735–738. *Hydrangea arborescens* and *Panax ginseng* extracts have been used in maintaining the health of the prostate, Simon, H B, (2000) Harvard Mens Health Watch. 4(9):8. *Panax ginseng* has also been shown to reduce the prostatic weight in male rats while increasing blood testosterone levels. Fahim M S. Fahim Z. Harman J M. Clevenger T E. Mullins W. Hafez E S. (1982) Archives of Andrology. 8(4):261–3, 1982 June.

Vitamin B6, along with zinc has been associated with a reduced risk of prostatic cancer. Key T J. Silcocks P B. Davey G K. Appleby P N. Bishop D T. (1997) Brit. J. Cancer. 76(5):678–87. Deficiency of Vitamin B6 may be associated with increased prostatic estradiol, that is known to sensitize it to steroidal hormonal effects. Bender D A, Ghartey-Sam K, Singh A. (1989) Brit. J. Nutrition, 61(3):619–28. Vitamin A is also believed to be a useful in the prevention of prostate cancer, Olson K B and Pienta K J. (1998) J. Nat. Cancer Institute. 90(6):414–5. Copper has been shown to reduce levels of plasma testosterone and several of the enzymes involved in its production. Chattopadhyay A. Sarkar M. Sengupta R. Roychowdhury G. Biswas N M. (1999) J. Toxicological Sciences. 24(5):393–7.

Currently, methods of treatment for BPH and prostatic cancers include surgery, radiation therapy, and chemotherapy. The two most common operations for prostate cancer are radical prostatectomy and transurethral resection of the prostate (TURP). Radical prostatectomy removes the entire prostate gland and some tissue around it and carries a high risk of impotence and incontinence following surgery. The radical prostatectomy operation lasts from 1.5 to 4 hours, followed by an average hospital stay of three days and an average time away from work of three to five weeks. The TURP procedure last about 1 hours, followed by an average hospital stay of 1–2 days and 1–2 weeks time away from work and also has the adverse side effect of loss of bladder control. The side effects of radiation therapy can include diarrhea and irritated intestines, frequent urination, burning while urinating and blood in the urine, and a feeling of tiredness. Side effects of chemotherapy can include nausea and vomiting, loss of appetite, loss of hair, and mouth sores. Chemotherapy can also effect blood cells, which can increase the chance of infection, bleeding or bruising after minor injuries, as well as tiredness. Thus, alternative, non-invasive, treatments of BPH and prevention of prostate cancer are needed which have low toxicity and few side effects.

SUMMARY OF THE INVENTION

The present invention provides a composition of herbs and their extracts for treatments of BPH and the symptoms thereof and the prevention of prostate cancer. The present invention also provides a composition to effectively reduce micturitional disorders including prostate volume, residual urine, frequency of urination, and to improve urine flow rate, and balance hormone levels. This invention can also be used as a dietary supplement to prevent BPH and prostate cancer.

The composition comprises lycopene, *Serenoa repens, Pygeum africanum,* and *Urtica dioica*, or extracts thereof. The composition to be administered may be prepared with any dose preparation in the art, including alcohol extracts, powders, mixing and encapsulation, and is not limited to any particular form. The components of the composition may be added in any order without limitation. More preferably the composition of the present invention comprises, by weight,: lycopene in an amount from about 0.1 to 10%, *Serenoa repens* in an amount from about 30 to 60%, *Pygeum africanum* in an amount from about 4 to 25%, and *Urtica dioica* in an amount from about 30 to 60%.

The invention further provides a method of treating BPH and prostate cancer or at least alleviate their symptoms in an subject in need thereof which comprises administering a therapeutic amount of the composition described herein.

The present invention ameliorates at least some of the disadvantages or the prior art therapies and methods, or at least provides a useful alternative. The availability of the herbs and the ease of formulation (powdering, extractions, etc) provides a less costly alternative medicament. The treatment may also be individualized as well as prepared by standard formulation, making the treatment more broadly applicable and effective over both short and long term administration.

These and other features, aspects, and advantages of the present invention will become better understood with regard to the following detailed description and accompanying claims.

DETAILED DESCRIPTION

The composition of this invention includes a combination of the herbs, *Serenoa repens, Pygeum africanum,* and *Urtica dioica,* or extracts thereof, and the pytochemical lycopene, which were specifically chosen and combined according to their biological activities. The term "herb" as used herein refers to the whole herb or tuber, or to the seeds, leaves, stems, flowers, roots, berries, bark, or any other plant parts that are used for healing.

The lycopene component of the composition was obtained is available commercially from Hoffman La Roche, of Nutley, N.J., U.S.A, as a synthetic chemical available at a 5% strength that is chemically identical to the lycopene extracted from tomato fruit using standard methods. The natural standardized extract is available from many sources well known to those of ordinary skill in the art at a strength of 3%, including Brainway, Inc., Senovazne 23, Praha 1, 110 Czech Republic.

The *Serenoa repens* component of the composition is available commercially around the world, through distributors such as Amira, Box 1717, Alachua Fla., U.S.A. The component is obtained from the Berry portion of the herb and the component is preferably powdered but may also be cut, and preferably contains about 40% fatty acids.

The *Pygeum africanum* component of the composition is available commercially around the world, through distributors, such as Advanced Alternatives for Better Health, 1344 Lansing Avenue, Lansing Mich., U.S.A. Preferably, the powdered bark is used and contains about 2.0–2.5% steroids.

The *Urtica dioca* component of the composition is available commercially around the world, through distributors such as Advanced Alternatives for Better Health, 1344 Lansing Avenue, Lansing Mich. 48915 and Amira, Box 1717, Alachua Fla., U.S.A. The preferred embodiment of the invention contains the component from the powdered root, with 0.8% sterols, but alternatively the root may be cut or powdered or cut leaves may be utilized.

The methods for combining the herbs, extracts, and vitamins are well known to those of ordinary skill in the art and may be accomplished at a number of commercial production laboratories around the world.

Each herbal component selected in this group has been well characterized and used individually before for the treatment of BPH and for the prevention of prostate cancer. However, they have not, to date, been used together as is disclosed in this invention. It is the synergism between all of the herbs that renders the administration of a combination containing each of the herbs desirable. As a holistic approach to combating the treatment of BPH and prevention of prostate cancer, herbs were selected which possess the following biological activities: (1) anti-tumor activity; (2) immune stimulating activity; (3) anti-androgen activity; (4) anti-BPH activity; and (5) activities to restore micturitional disorders. Most of the herbs have multi functional activities.

In a specific embodiment of the invention, the composition comprises between 0.1 and 180 mg lycopene, an amount that will comprise from 0.1 to 10% by weight of a tablet or capsule having a total weight of 100 to 1800 mg, between 30 and 1080 mg *Serenoa repens*, an amount that will comprise from 30 to 60% by weight of a tablet or capsule having a total weight of 100 to 1800 mg, between 4 and 450 mg *Pygeum africanum*, and amount that will comprise from 4 to 25% by weight of a tablet or capsule having a total weight of 100 to 1800 mg, and between 30 and 1080 mg *Urtica dioica*, an amount that will comprise from 30 to 60% by weight of a tablet or capsule having a total weight of 100 to 1800 mg.

In yet another embodiment of the invention, the composition comprises between 0.1 and 60 mg lycopene, an amount that will comprise from 0.1 to 10% by weight of a tablet or capsule having a total weight of 100 to 600 mg, between 30 and 360 mg *Serenoa repens*, an amount that will comprise from 30 to 60% by weight of a tablet or capsule having a total weight of 100 to 600 mg, between 4 and 150 mg *Pygeum africanum*, and amount that will comprise from 4 to 25% by weight of a tablet of capsule having a total weight of 100 to 600 mg, and between 30 and 360 mg *Urtica dioica*, an amount that will comprise from 30 to 60% by weight of a tablet or capsule having a total weight of 100 to 600 mg. In yet another embodiment of the invention, the composition comprises about 50 mg lycopene, about 150 mg *Serenoa repens*, about 50 mg *Pygeum africanum*, and about 150 mg *Urtica diocia*.

In a preferred embodiment, the composition further comprises between about 3 and 3 mg Vitamin A; between about 5 and 150 mg Vitamin B6; between about 1 mg and 25 mg zinc; between about .1 and 5 mg copper; between about 10 mg and 600 mg bee pollen powder; between about 10 mg and 1800 mg each of the amino acids alanine, glutamine, and glycine; between about 5 mg and 500 mg *Panax ginseng* extract; and between about 1 and 100 mg *Hydrangea arborescens* extract. In yet another embodiment, the composition further comprises between 1 and 2 mg Vitamin A, between 5 and 50 mg Vitamin B6, between 1 and 15 mg zinc, between 0.1 and 2 mg copper, between 10 mg and 240 mg Bee pollen powder, between 10 and 600 mg each of alanine, glutamine, and glycine, between 5 and 100 mg *Panax ginseng* extract and between 1 and 25 mg *Hydrangea arborescens* extract. In yet another embodiment, the composition further comprises about 1.5 mg Vitamin A, about 15 mg Vitamin B6, about 5 mg Zinc, about 0.5 mg Copper; about 60 mg Bee pollen powder, about 60 mg each of Alanine, Glutamine, and Glycine, about 10 mg *Panax ginseng* extract, and about 5 mg *Hydrangea arborescens* extract.

In a more preferred embodiment the composition is present in a 500 mg tablet or capsule containing about 50 mg lycopene, an amount that will comprise about 10% by weight of the tablet or capsule, about 150 mg *Serenoa repens*, and amount that will comprise about 30% by weight of the tablet or capsule, about 50 mg *Pygeum africanum*, an amount that will comprise about 10% by weight of the tablet or capsule, and about 150 mg *Urtica dioica*, and amount that will comprise about 30% by weight of the tablet or capsule, and about 1.5 mg Vitamin A, about 15 mg Vitamin B6, about 5 mg Zinc, about 0.5 mg Copper, about 60 mg bee pollen powder, about 60 mg each of alanine, glutamine, and glycine, about 10 mg *Panax ginseng* extract, and about 5 mg *Hydrangea arborescens* extract.

In a further embodiment, the composition is administered in four tablets, each comprising about 500 mg red yeast rice, about 15 mg coenzyme $Q_{10}$, about 50 mcg chromium, about 13 mg inositol, about 50 mcg selenium, and about 20 IU mixed tocopherols to provide a total daily dose of about 2 gm red yeast rice, about 60 mg Coenzyme $Q_{10}$, about 200 mcg chromium, about 52 mg inositol, about 200 mcg selenium and about 80 IU mixed tocopherols.

Preferably, the compositions of the present invention are prepared in a tablet dosage form, however it will be understood by those skilled in the art that other dosage forms may also be suitably prepared by known methods, for example, capsules, caplets, powders, pastes, liquids and similar dosage forms. Also, it will be understood that the compositions may also contain one or more conventional pharmaceutically acceptable excipients, adjuvants, solvents or carriers and may also include flavors, colorings, coatings, etc.

One dose of the pharmaceutical composition for the treatment of BPH, for example one tablet or one capsule, may contain, for example 100–600 mg of the composition of the present invention. One dose of the pharmaceutical composition for the prevention of prostatic cancers may contain, for example, 600–1800 mg of the composition of the present invention. The compositions are preferably administered in spaced dosages throughout the day, for example, administered every three to six hours, so as to maintain the level of active ingredients in the system of the mammal. The dose may be administered in single or divided doses throughout the day and is preferably taken with food.

A person skilled in the art will understand that the therapeutic effects of the compositions result from a plurality of active agents in each herb which when combined, act synergistically to enhance efficacy. It will also be understood that the compositions comprising all agents, are also contemplated herein, as are liquid or slow release formulations of the composition. Thus, it will be understood that the compositions of the invention can be administered orally, rectally (as suppositories), intravenously, topically or by other known means. As a capsule, the formulation should be stored at a temperature of 80° or less.

The administration of the composition would be in accordance with a predetermined regimen, which would be at least once daily and over an extended period of time as a chronic treatment, and could last for one year or more, including the life of the host. The dosage administered will depend upon the frequency of the administration, the blood level desired, other concurrent therapeutic treatments, the severity of the condition, whether the treatment is for prophylaxis or therapy, the age of the patient, the levels of LDL-cholesterol and HDL-cholesterol in the patient, and the like.

The following examples will serve to further typify the nature of the invention, but is not limited on the scope thereof, which is defined solely by the appended claims.

EXAMPLE 1

Tablets, each containing the following compositions.
Composition for treatment of BPH (for 1000 tablets)

| | |
|---|---|
| Lycopene | 0.4 g. |
| Serenoa repens | 150 g. |
| Pygeum africanum | 50 g. |
| Urtica dioica | 50 g. |

EXAMPLE 2

Tablets, each containing the following compositions.
Composition for prevention of prostate cancer (for 1000 tablets)

| | |
|---|---|
| Lycopene | 0.4 g. |
| Serenoa repens | 150 g. |
| Pygeum africanum | 50 g. |
| Urtica dioica | 150 g. |

EXAMPLE 3

Capsule, each containing the following compositions.

| | |
|---|---|
| Vitamin A | 5,000 IU |
| Vitamin B6 | 15 mg |
| Zinc (as arginate) | 5 mg |

-continued

| | |
|---|---|
| Copper (as gluconate) | 0.5 mg |
| Urtica dioica extract (root, 0.8% sterols) | 150 mg |
| Serenoa repens extract (berry, 40% fatty acids) | 150 mg |
| Bee pollen powder | 60 mg |
| L-Alanine | 60 mg |
| L-Glutamic acid | 60 mg |
| L-Glycine | 60 mg |
| Pygeum africanum extract (bark, 2.0–2.5% sterols) | 50 mg |
| Panax ginseng extract (root, 25% ginsenosides) | 10 mg |
| Lycopene (5%) | 50 mg |
| Hydrangea arborescens extract (root, 4:1) | 5 mg |

The following references are incorporated herein by reference: U.S. Provisional Application No. 60/153,322; Kupelian P A, et al., (1997) J. of Urol 158(6):2197–2201; Carter B S, et al., (1992) Proc Natl Academy Science USA 89:3367–3371; Walsh P C, Partin A W, (1997) Cancer 80:1871–74; Cooney K A, et al., (1997) Natl Cancer Inst 89:955–959; Smith J R, et al., (1996) Science 274:1371–1374; Gronberg H, et al., (1999) Am J of Hum Genet 65(1):134–140; Li J, et al., (1997) Science 275:1943–1947; Perrin P, et al., (1991) Presse Med 20(28): 1313–1319; Harvey, H, (1995) Pathol Res Prac 191(9): 924–934; Gann P H, et al., (1999) Cancer Res 59(6): 1225–1230; Giovannucci E, (1999) J Natl Cancer Inst 91(4):317–331; Rao A V, et al., (1999) Nutr Cancer 33(2): 159–164; Pastori M, et al., (1998) Biochem Biophys Res Commun 250(3):582–585; Bayne C W, et al., (1999) Prostate 40(4):232–241; Wilt T J, et al., (1998) JAMA 280(18): 1604–1609 ; Delos S, et al., (1995) J Steroid Biochem Mol Biol 55(3–4):375–383; Schroder F, (1994) Clin Endocrinol 41(2):139–147; Barlet A, et al., (1990) Wien Klin Wochenschr 22:667–673; Carani C, et al., (1991) Arch Ital Urol Nefrol Androl 63:341–345; Varro, T. *Herbs of Choice*, (1994) Pharmaceutical Press; Schottner M, et al., (1997) Planta Med 63(6):529–532; Hryb D J, et al., (1995) Planta Med 61(1):31–32; Mindell, E., Earl Mindell's Herb Bible, A Fireside Book (1992); Rosner W, et al., (1999) J Steroid Biochem Mol Biol 69(1–6):481–485; Damrau, F. (1958) J. Maine Medical Association 49:99–102; Aito, K. & Iwatsubo, E. (1972) Hinyokika Kiyo—Acta Urologica Japonica. 18(1):41–4); Feinblatt, H M & Gant, J (1958), J Maine Medical Assoc. 49:99–124; Mahajan, S K, et al. (1982), Amer J Clin Nutr 36: 1177–1183; Leake, Chisholm & Harib (1984), J Steroid Biochem 20:651–655; Fahim, Wang Sutcu & Fahim (1993), Andrologia 25:369–75; Antoniou, Sudhakar, Shalhoub & Smith (1977), Lancet Oct.: 895–898; Wallace, A M, & Grant, J K (1975) Biochemical Society Transactions 3:540–542; Buck A C, Rees, R W M, Ebeling, L (1989), Brit J Urology 64:496–499; Rugendorff, E W et.al. (1993), Brit J. Urology 71:433–438; Habib, F K (1990), Brit J Urology 66:393–397; Zhang, X (1995) J Med Chem 38: 735–738; Simon, H B, (2000) Harvard Mens Health Watch. 4(9):8; Fahim M S. Et al., (1982) Archives of Andrology. 8(4):261–3, 1982 June; Key T J., et al., (1997) Brit. J. Cancer. 76(5):678–87; Bender D A, Ghartey-Sam K, Singh A. (1989) Brit. J. Nutrition, 61(3):619–28; Olson K B and Pienta K J. (1998) J. Nat. Cancer Institute. 90(6):414–5; and Chattopadhyay A., et al., (1999) J. Toxicological Sciences. 24(5):393–7.

What is claimed is:

1. A composition for treating benign prostate hypertrophy comprising effective amounts of lycopene and the herbs *Serenoa repens*, *Pygeum africanum*, and *Urtica dioica*.

2. The composition of claim 1, further comprising the amino acids glycine, arginine and glutamine.

3. The composition of claim 2 wherein the amino acids are present in the form of L-glycine, L-arginine, and L-glutamic acid.

4. The composition of claim 2 wherein the amino acids are each present in an amount between 10 mg and 1800 mg.

5. The composition of claim 4 wherein the amino acids are each present in an amount between 10 mg and 600 mg.

6. The composition of claim 5 wherein the amino acids are each present in an amount of about 60 mg.

* * * * *